(12) United States Patent
Yi et al.

(10) Patent No.: US 9,572,513 B2
(45) Date of Patent: Feb. 21, 2017

(54) DEVICE FOR MEASUREMENT FOR BIONIC INFORMATION HAVING HAND REST

(75) Inventors: Sung Il Yi, Seoul (KR); Ki Young Kim, Bucheon (KR); Kang Eun Kim, Seoul (KR); Chang Heon Kang, Ansan (KR)

(73) Assignee: KOREA INSTITUTE OF INDUSTRIAL TECHNOLOGY, Cheonan-si (KR)

(*) Notice: Subject to any disclaimer, the term of this patent is extended or adjusted under 35 U.S.C. 154(b) by 0 days.

(21) Appl. No.: 13/394,886

(22) PCT Filed: Sep. 8, 2010

(86) PCT No.: PCT/KR2010/006108
§ 371 (c)(1),
(2), (4) Date: Mar. 8, 2012

(87) PCT Pub. No.: WO2011/031062
PCT Pub. Date: Mar. 17, 2011

(65) Prior Publication Data
US 2012/0172729 A1 Jul. 5, 2012

(30) Foreign Application Priority Data

Sep. 8, 2009 (KR) .................. 10-2009-0084496
Sep. 8, 2009 (KR) .................. 10-2009-0084499

(51) Int. Cl.
| A61B 5/02 | (2006.01) |
| A61B 5/053 | (2006.01) |
| A61B 5/024 | (2006.01) |
| A61B 5/00 | (2006.01) |

(52) U.S. Cl.
CPC ............. *A61B 5/0537* (2013.01); *A61B 5/024* (2013.01); *A61B 5/4872* (2013.01); *A61B 5/6825* (2013.01)

(58) Field of Classification Search
CPC .......................... A61B 5/024; A61B 5/6825
USPC ........................... 600/483, 504, 513
See application file for complete search history.

(56) References Cited

U.S. PATENT DOCUMENTS

| 3,935,984 | A | * | 2/1976 | Lichowsky et al. | 600/499 |
| 5,615,672 | A | | 4/1997 | Braig et al. | |
| 7,057,604 | B2 | * | 6/2006 | Bajramovic | 345/163 |
| 2001/0000526 | A1 | * | 4/2001 | Gopinathan et al. | 600/300 |
| 2001/0034491 | A1 | * | 10/2001 | Benson et al. | 600/547 |
| 2001/0056227 | A1 | * | 12/2001 | Gopinathan et al. | 600/300 |

(Continued)

FOREIGN PATENT DOCUMENTS

| JP | 06-125881 A | 5/1994 |
| JP | 11033007 A | 2/1999 |

(Continued)

*Primary Examiner* — Christian Jang
(74) *Attorney, Agent, or Firm* — Patent Office of Dr. Chung Park (57) ABSTRACT

There is disclosed an apparatus for measuring biometric information having a hand rest, which can perform precise and comprehensive measurement by measuring biometric information about an examinee taking a more comfortable position. The apparatus for measuring the biometric information having the hand rest formed in a convex curvature shape to have an examinee's hand put thereon, to contact with an examinee's palm and fingers; and a measurement part provided in the hand rest to measure the examinee's biometric information.

7 Claims, 6 Drawing Sheets

(56) References Cited

U.S. PATENT DOCUMENTS

| | | | | |
|---|---|---|---|---|
| 2003/0032869 A1* | 2/2003 | Muramatsu | ............ | A61B 5/022 600/300 |
| 2005/0065442 A1* | 3/2005 | Hashimoto | ............ | A61B 5/021 600/501 |
| 2008/0208018 A1 | 8/2008 | Ridder et al. | | |

FOREIGN PATENT DOCUMENTS

| | | |
|---|---|---|
| JP | 2001-187029 A | 7/2001 |
| JP | 2005087483 A | 4/2005 |
| KR | 10-2001-0093524 A | 10/2001 |

* cited by examiner

DEVICE FOR MEASUREMENT FOR BIONIC INFORMATION HAVING HAND REST

CROSS-REFERENCE TO PRIOR APPLICATIONS

This application is a national Stage Patent Application of PCT International Patent Application No. PCT/KR2010/006108, filed on Sep. 8, 2010 under 35 U.S.C. §371, which claims priority of Korean Patent Application Nos. 10-2009-0084496, filed on Sep. 8, 2009 and 10-2009-0084499 filed on Sep. 8, 2009 which are all hereby incorporated by reference in their entirety.

TECHNICAL FIELD

Embodiments of the invention may relate to an apparatus for measuring biometric information, more particularly to, an apparatus for measuring biometric information that can perform precise and comprehensive measurement by measuring biometric information about an examinee taking a more comfortable position.

BACKGROUND

Recently, there have been increasing concerns and demands for medical check-up, as the living standard and health-consciousness are improving. In a typical medical check-up, a blood pressure, a pulse wave, an electrocardiogram (EKG) and body fat are measured and utilized as basic data.

For that, each of medical offices is equipped with a sphygmomanometer for measuring the blood pressure, an electrocardiograph for measuring the electrocardiogram, a body fat meter for measuring the body fat, a pressurized sphygmograph for measuring the pulse wave and a plethysmograpy for measuring the blood flow rate.

However, conventional measuring devices have following disadvantages.

First of all, a single apparatus measures one piece of biometric information and different measuring devices have to be provided to measure a variety of human information. This requires too much unnecessary space and it is difficult to repair and maintain the apparatuses. Also, an examinee has to move from one device to another device to have the measurement and he or she has inconvenience.

Second, a single device measures a single type of biometric information. Accordingly, the measured biometric information fails to be collected and it has to be inputted and utilized by a human resource. When collecting the biometric information, an error or a mistake might be generated disadvantageously.

Third, clippers having an electron installed thereon pick up a measuring area such as a finger before measurement in a conventional body fat measuring device or an electrocardiogram device. The clippers are connected with a body via a wire and the wire has concern of being twisted. Also, when examining himself or herself, it is not easy for a user to pick up another finger after picking up one of fingers alone.

DISCLOSURE

Technical Problem

To solve the problems, an object of the embodiments is to provide an apparatus for measuring biometric information including a hand rest, which can measure a variety of biometric information as single device.

Technical Solution

To achieve these objects and other advantages and in accordance with the purpose of the embodiments, as embodied and broadly described herein, an apparatus for measuring biometric information having a hand rest formed in a convex curvature shape to have an examinee's hand put thereon, to contact with an examinee's palm and fingers; and a measurement part provided in the hand rest to measure the examinee's biometric information.

A finger seating recess formed in a corresponding shape to each of human fingers may be provided in the hand rest to seat the examinee's finger thereon.

The biometric information measured by the measurement part may be at least one of an electrocardiogram, body fat and a plethysmogram.

The measurement part may be a plethysmogram sensor provided in a predetermined position of the finger seating recess to contact with the examinee's fingers, to measure blood flow variation of the examinee's fingers, the plethysmogram sensor including an infrared ray emitting part and an infrared ray receiving part.

The measurement part may be an electrocardiogram measuring unit configured to measure the examinee's electrocardiogram.

Two hand rests may be provided corresponding to the examinees' right and left hands, respectively, and the electrocardiogram measuring unit may include a first electrocardiogram sensor and a second electrocardiogram sensor provided in palm and finger contactable portions of one of the two hand rests corresponding to the examinee's left and right hands, respectively; and a third electrocardiogram sensor provided in a palm or finger contactable portion of the other one of the two hand rests corresponding to the examinee's left and right hands, and the electrocardiogram measuring unit may sense electric activity generated in the examinee's heartbeat.

The measurement part may be a body fat measuring unit configured to measure the examinee's body fat.

Two hand rests may be provided corresponding to the examinee's right and left hands, respectively, and the body fat measuring unit may include a first body fat sensor and a second body fat sensor provided in finger contactable portions of one of the two hand rests corresponding to the examinee's right and left hands, each of the first body fat sensor and the second body fat sensor that is able to contact with a different finger; and a third body fat sensor and a fourth body fat sensor provided in finger contactable portions of the other one of the two hand rests, each of the third and fourth body fat sensors that is able to contact with a different finger, and the body fat measuring sensor may measure the examinee's body fat.

Advantageous Effects

The embodiments have following advantageous effects.

First, the measuring unit to measure biometric information is provided in the mouse-shaped hand rest easy to put the examinee's hand, not in a clipper-type. Accordingly, clippers-picking-up activity is unnecessary and the examinee's convenience may be enhanced effectively.

Second, the various types of the measuring units are provided and various types of biometric information can be achieved. Without various measurement equipments, the cost for equipping the measurement equipments can be reduced and convenience in repair and maintenance may be enhanced. Also, plural measuring devices need not be provided and less space is required. Moreover, a variety of biometric information can be acquired at one time and convenience of the examination can be enhanced. The acquired information is automatically collected and mistakes that might be generated by errors can be reduced. Different types of biometric information can be fused smoothly.

BRIEF DESCRIPTION OF THE DRAWINGS

Arrangements and embodiments may be described in detail with reference to the following drawings in which like reference numerals refer to like elements and wherein.

BEST MODE

As follows, embodiments will be described in detail to be embodied by those skilled in the art to which the embodiments pertain to, in reference to the accompanying drawings. Reference may now be made in detail to specific embodiments, examples of which may be illustrated in the accompanying drawings. Wherever possible, same reference numbers may be used throughout the drawings to refer to the same or like parts.

Figure 1:
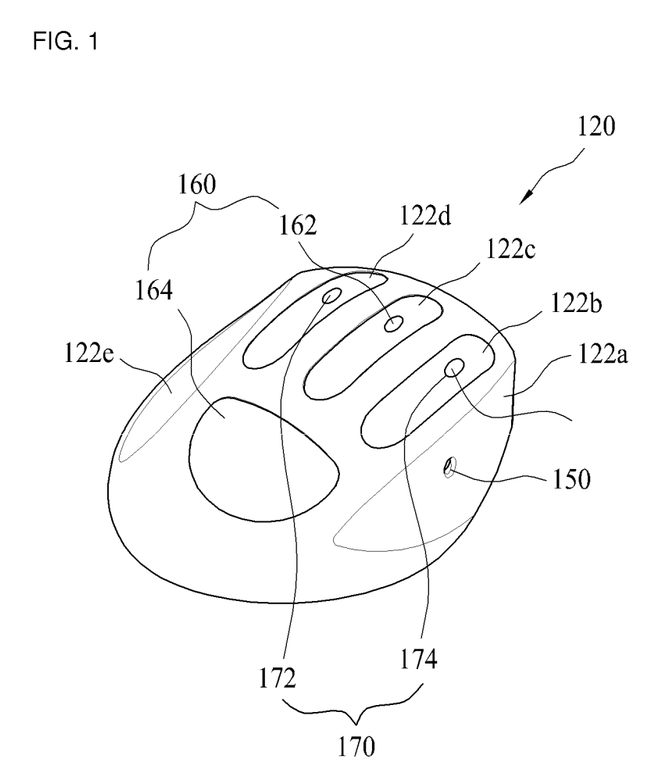
FIG. 1 is a perspective view illustrating an apparatus for measuring biometric information according to an embodiment of the invention.
Figure 2:
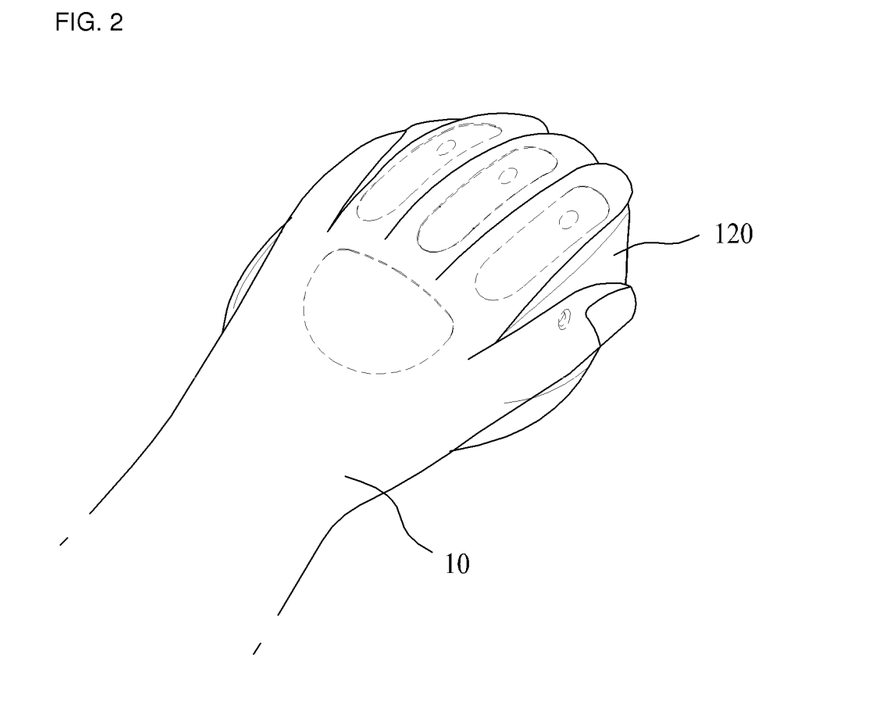
FIG. 2 is a perspective view illustrating the apparatus shown in FIG. 1 that has an examiner's hand seated thereon.

As shown in FIGS. 1 and 2, an apparatus for measuring biometric information (hereinafter, a biometric measuring apparatus) including a hand rest according to this embodiment includes a hand rest 120 and a measuring part.

The hand rest 120 is formed in a convex curvature shape similar to a mouse for a computer to put an examinee's hand 10 thereon and it has an appearance that can be held by the examinee's hand 10 put on a surface thereof lightly, to contact with the examinee's palm and fingers.

Also, finger seating recesses 122a~122e may be formed in a surface of the hand rest 120 to seat each finger of the hand put on the hand rest 120, in corresponding shapes to human fingers.

Also, not shown in the drawings, the hand rest 120 may include a transmitting port (not shown) that is able to be connected with an external device such as an external analyzer, a monitor or a storage device via a cable or wirelessly. Also, the hand rests 120 may be connected with each other via the transmitting port (not shown).

Meanwhile, the measurement part is a component configured to measure the examinee's biometric information and it is provided in the housing 110 or the hand rest 120. The measurement part may be at least one of a plethysmogram measuring unit 160, an electrocardiogram measuring unit 170 and a body fat measuring unit 170.

In this instance, the expression of "at least one of" means one or more than two.

Of course, another type of a measuring unit may be provided, rather than those measuring units.

The plethysmogram measuring unit 150 is a component configured to measure a blood flow rate of the blood flowing to a top of a finger and a pulse waveform.

The plethysmogram measuring unit 150 is a photo sensor that measures a blood flow rate of the blood flowing to a peripheral portion and a pulse waveform and it includes a plethysmogram sensor 150. The plethysmogram sensor 150 includes an infrared ray emitting part and an infrared ray receiving part that are provided in the finger seating recess 122 where the finger seated on the hand rest 120 is positioned to measure the blood flow rate of the blood flowing to the peripheral portion and the pulse waveform.

Preferably, as shown in FIGS. 1 and 2, the plethysmogram sensor 150 may be provided in the finger seating groove 122a where a thumb is seated.

Figure 3:
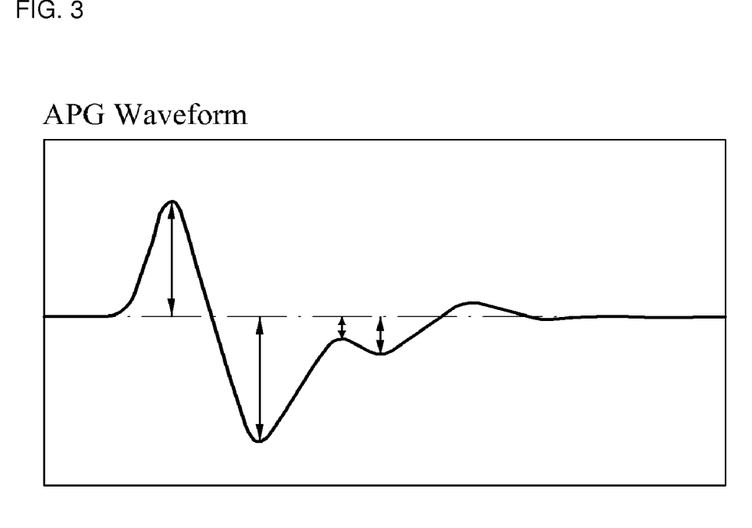
FIG. 3 is a diagram illustrating a graph of accelerated plethysmogram gained by a plethysmogram measuring device shown in FIG. 1.

The information gained by the plethysmogram measuring unit 150 may include the minute-based heartbeat, the heart rate variable (HRV) and accelerated plethysmogram (APG) as shown in FIG. 3. Also, a cardiovascular disease such as a vaso-aging degree and blood circulatory disturbance may be diagnosed in good time based on a pattern of the accelerated plethysmogram measured by the plethysmogram sensor 150.

Figure 4:
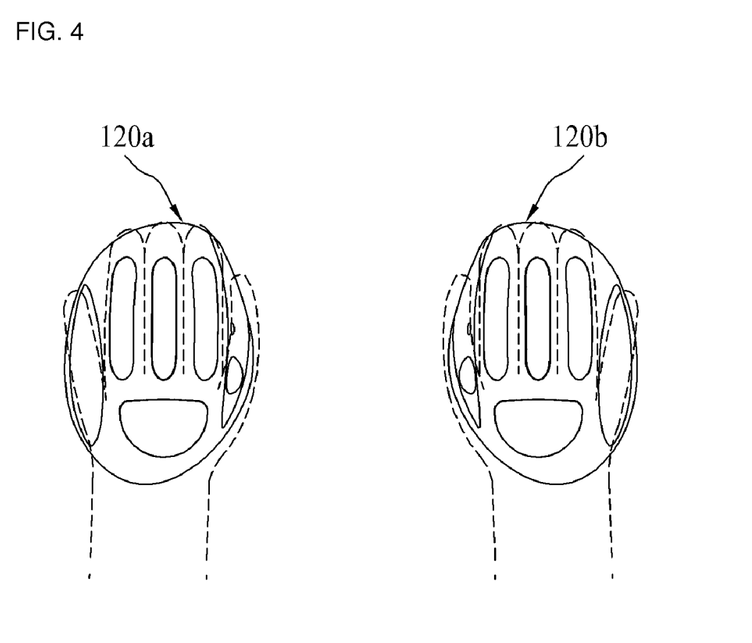
FIG. 4 is a plane view illustrating two apparatuses for measuring biometric information for right and left hands.

Meanwhile, when the measurement part includes an electrocardiogram measuring unit, the biometric information measuring apparatus 100 may include two pairs of housings and hand rests corresponding to the right and left hands, as shown in FIG. 4.

"Electrocardiography (EGG)" means a record of electric activity generated in the heart whenever the heart beats. After electrons are attached to a predetermined area of an examinee's skin, electrons are combined variously and electrocardiogram signals are recorded in a storage device.

According to this embodiment, augmented lead that measures and records heart activity in three directions may be used to amplify a minute human voltage gained from an electron. The augmented lead is a unipolar lead. Out of three leads, one lead has a positive polarity and the other two leads have a negative polarity. Displacement of the heart in a positive-polarized augmented area is amplified and utilized.

Generally, when using three electrons, electrons are attached to both hands and a foot. In this embodiment, electrons are in contact with the fingers and the palm of both hands, to improve measuring efficiency.

Electrons of the electrocardiogram measuring unit 160 may be provided in the hand rest 120. More specifically, a first electrocardiogram sensor 162 and a second electrocardiogram sensor 164 may be provided in palm and finger contactable portions in one of the hand rests 120 corresponding to the right and left hands. A third electrocardiogram sensor (not shown) may be provided in a palm or finger contactable portion in the other one of the hand rests 120 corresponding to the right and left hands.

Figure 5:
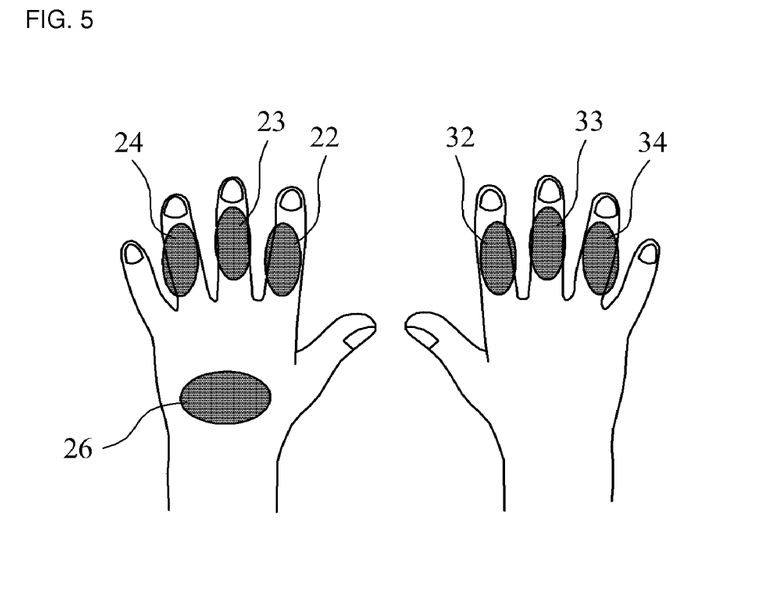
FIG. 5 is a plane view illustrating an area of a hand contacting with a electrocardiogram measuring device of the apparatus for measuring the biometric information shown in FIG. 1.

According to this embodiment, as shown in FIGS. 1 and 5, the first electrocardiogram sensor 162 may be provided in a finger seating recess 122c of a left hand rest 120a to contact with a middle finger 23 of the left hand and the second electrocardiogram sensor 164 may be provided in a surface of the hand rest 120 to contact with a palm 26 of the left hand. The third electrocardiogram sensor (not shown) may be provided in a finger seating recess of a right hand rest 120a to contact a middle finger 33 of the right hand.

The structure of the hand rests for the right and left hand are in symmetry and detailed description for the hand rests for the right and left hands will be omitted. Anyone skilled in the art may expect the structure without any problems The electrocardiogram measuring unit 160 having the above structure is able to measure a minute-based heartbeat in real time and a hear rate variable (HRV) during a predetermined time period can be measured based on the measured minute-based heartbeats. This is related to activities of the sympathetic nervous system and the parasympathetic nervous system. A stress degree may be estimated based on the measured HRV.

Meanwhile, when the measurement part includes the body fat measuring unit 170, the biometric information measuring apparatus 100 may include a pair of hand rests (120a and 120b) corresponding to the right and left hands, like the measurement part including the electrocardiogram measuring unit shown in FIG. 4.

Figure 6:
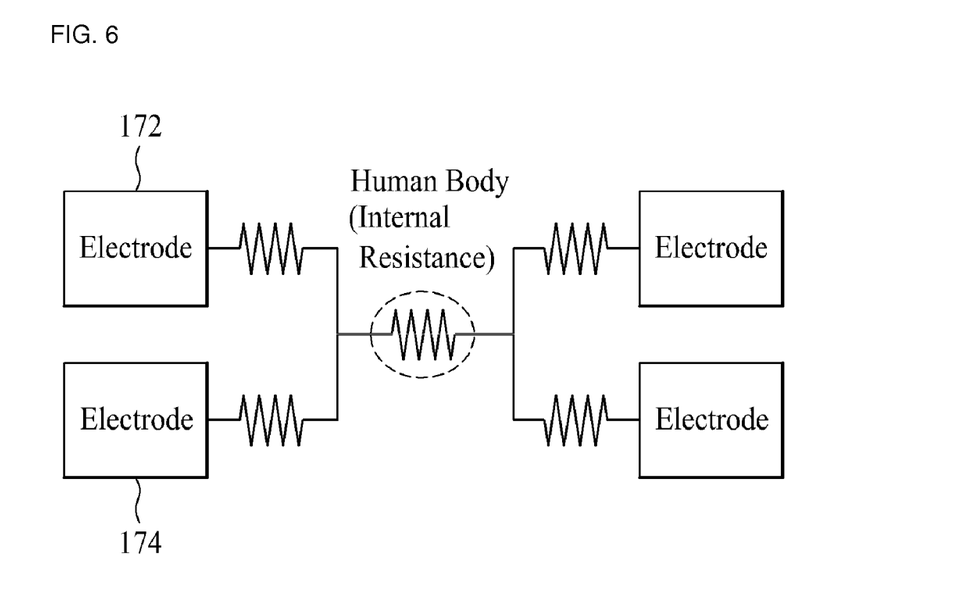
FIG. 6 is a diagram schematically illustrating a principle of measuring a body fat used by the apparatus for measuring the biometric information shown in FIG. 1.

As shown in FIG. 6, body fat measurement may be measured by analyzing resistance variation generated in the human body when currents are flowing to four electrons for two for each of the hands in contact with fingers of both hands as a bridge concept.

The electrons of the body fat measuring unit 170 may be provided in the hand rests 120. More specifically, as shown in FIG. 5, the electrons may contact with index fingers 22 and 32 and ring fingers 24 and 34 of the right and left hands. Accordingly, as shown in FIG. 1, a first body fat sensor 172 and a second body fat sensor 174 may be provided in finger seating recess 122b and 122d corresponding to the index and ring fingers in the left hand rest 120a, respectively. A third body fat sensor (not shown) and a fourth body fat sensor (not shown) may be formed in finger seating recesses (not shown) corresponding to index and ring fingers in the right hand rest 120b, respectively.

Meanwhile, the data gained by the plurality of the measuring units may be fused with each other, to generate new information. For example, a systolic and diastolic blood pressure value may be measured from a relation between a characteristic parameter of electrocardiographic signals and plethysmographic signals with the blood pressure.

Figure 7:
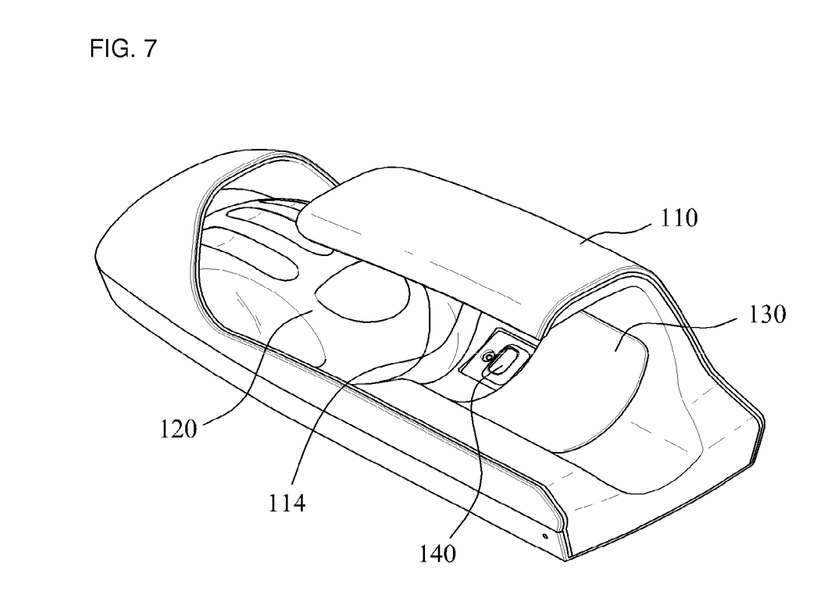
FIG. 7 is a perspective view illustrating a hand rest provided in the apparatus for measuring the biometric information that is provided in a housing.
Figure 8:
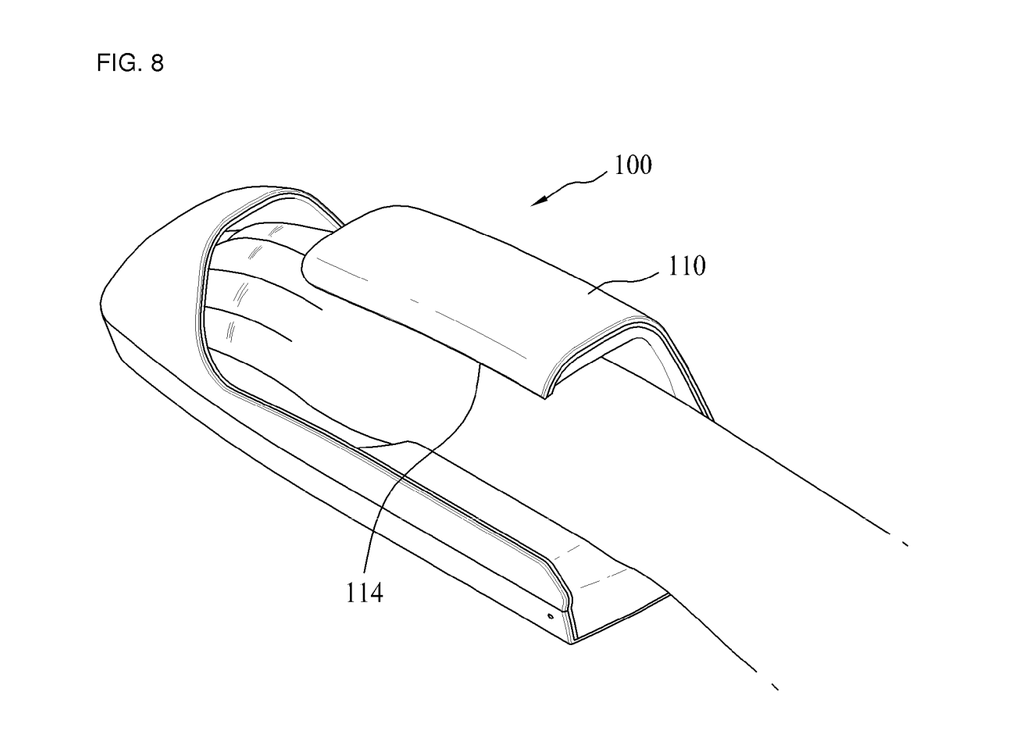
FIG. 8 is a perspective view illustrating a state of the examinee's forearm and hand seated in the apparatus shown in FIG. 7.
Figure 9:
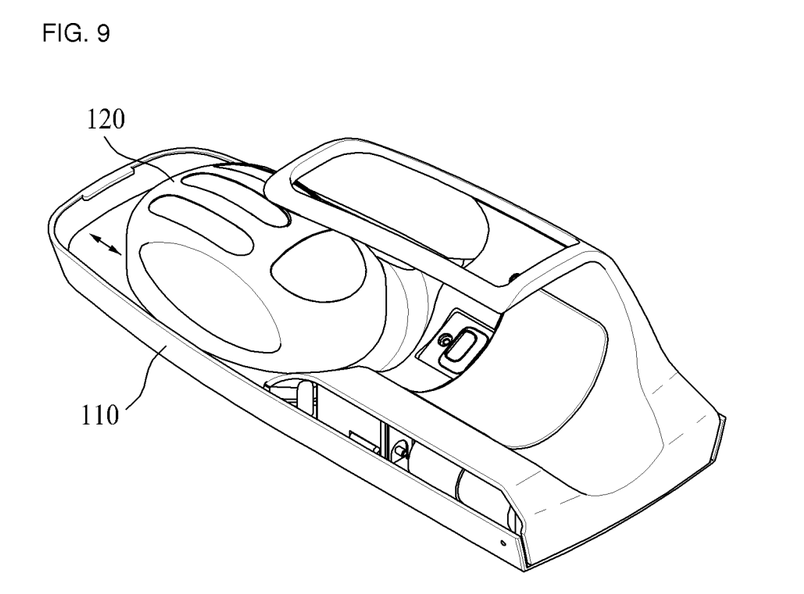
FIG. 9 is a perspective view illustrating the hand rest shown in FIG. 7 that is sliding with respect to the housing.

Meanwhile, the hand rest having the above structure may be provided in a housing as shown in FIGS. 7 and 8. The housing 110 forms a forearm seating part 112. The hand rest 120 is provided in front of the forearm seating part 112 of the housing 110.

A shoulder part of a human body between the elbow and the shoulder is called as 'the upper arm' and a part of a human body between the elbow and the wrist is called as 'the forearm'.

The forearm seating part 112 may be formed in an arc shape corresponding to the appearance of the examinee's forearm. Also, the housing 110 may have an approximately C-shaped appearance with an open side, to form a forearm introducing part 114 having an open portion to allow the examinee's forearm to be introduced into the forearm seating part 112 smoothly.

In inner surfaces of the forearm seating part 112 and the housing may be provided another biometric information measuring unit, rather than the plethysmogram measuring unit 150, the electrocardiogram measuring unit 160 and the body fat measuring unit 170. For example, a blood pressure measuring unit 130 or a pressurized pulse waveform measuring unit 140 may be provided.

Meanwhile, considering that everybody has a different length of the forearm, the hand rest 120 may be sliding forwardly and backwardly along a longitudinal direction of the forearm with respect to the housing 110, as shown in FIG. 4. Accordingly, the hand rest 120 can have an optimized position that can be adjustable for a person having a short forearm or a long forearm.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An apparatus for measuring biometric information comprising:
    a hand rest including a casing, a top surface of the casing having a convex curvature;
    a housing having a generally c-shape, forming a seating part for a palmar side of an examinee's forearm and covering a dorsal side of the examinee's forearm during operation;
    a measurement part provided in the hand rest and the housing to measure the examinee's biometric information, respectively and including at least one sensor; and
    the top surface of the casing including a finger seating recess configured to seat the examinee's finger thereon, the at least one sensor being disposed on the finger seating recess,
    wherein the hand rest which the examinee's finger is seated on is slidable along a longitudinal direction of the examinee's forearm with respect to the housing.

2. The apparatus for measuring the biometric information according to claim 1, wherein the biometric information measured by the measurement part includes at least one of an electrocardiogram, body fat and a plethysmogram.

3. The apparatus for measuring the biometric information according to claim 2, wherein the measurement part includes a plethysmogram sensor provided in a predetermined position of the finger seating recess to contact with the examinee's fingers, to measure blood flow variation of the examinee's fingers, the plethysmogram sensor comprising an infrared ray emitting part and an infrared ray receiving part.

4. The apparatus for measuring the biometric information according to claim 2, wherein the measurement part includes an electrocardiogram measuring unit configured to measure the examinee's electrocardiogram.

5. The apparatus for measuring the biometric information according to claim 4, wherein two hand rests are provided corresponding to the examinees' right and left hands, respectively, and
    the electrocardiogram measuring unit comprises,
    a first electrocardiogram sensor and a second electrocardiogram sensor provided in palm and finger contactable portions of one of the two hand rests corresponding to the examinee's left or right hand, respectively; and a third electrocardiogram sensor provided in a palm or finger contactable portion of the other one of the two hand rests corresponding to the examinee's left and right hands, and the electrocardiogram measuring unit senses electric activity generated in the examinee's heartbeat.

6. The apparatus for measuring the biometric information according to claim 2, wherein the measurement part includes a body fat measuring unit configured to measure the examinee's body fat.

7. The apparatus for measuring the biometric information according to claim 6, wherein two hand rests are provided corresponding to the examinee's right and left hands, respectively, and the body fat measuring unit comprises, a first body fat sensor and a second body fat sensor provided in finger contactable portions of one of the two hand rests corresponding to the examinee's right or left hand, each of the first body fat sensor and the second body fat sensor that is able to contact with a different finger; and a third body fat sensor and a fourth body fat sensor provided in finger contactable portions of the other one of the two hand rests, each of the third and fourth body fat sensors that is able to contact with a different finger, and the body fat measuring sensor measures the examinee's body fat.

* * * * *